(12) United States Patent
Lee et al.

(10) Patent No.: US 12,204,624 B2
(45) Date of Patent: Jan. 21, 2025

(54) USER AUTHENTICATION APPARATUS AND METHOD USING BRAINWAVE SIGNAL ACCORDING TO IMAGINED SPEECH

(71) Applicant: Korea University Research and Business Foundation, Seoul (KR)

(72) Inventors: Seong-Whan Lee, Seoul (KR); Young-Eun Lee, Seongnam-si (KR); Seo-Hyun Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 298 days.

(21) Appl. No.: 17/844,870

(22) Filed: Jun. 21, 2022

(65) Prior Publication Data

US 2022/0405370 A1 Dec. 22, 2022

(30) Foreign Application Priority Data

Jun. 21, 2021 (KR) ........................ 10-2021-0079992

(51) Int. Cl.
*G06F 21/32* (2013.01)
*A61B 5/00* (2006.01)
(Continued)

(52) U.S. Cl.
CPC .............. *G06F 21/32* (2013.01); *A61B 5/117* (2013.01); *A61B 5/374* (2021.01); *A61B 5/378* (2021.01);
(Continued)

(58) Field of Classification Search
CPC ........... G06F 21/32; G06F 3/015; A61B 5/38; A61B 5/374; A61B 5/378; A61B 5/117; A61B 5/7267
See application file for complete search history.

(56) References Cited

U.S. PATENT DOCUMENTS 10,819,703 B2 10/2020 Zhu
2019/0058703 A1* 2/2019 Zhu ........................ A61B 5/374
(Continued)

FOREIGN PATENT DOCUMENTS

JP 2004-248714 A 9/2014
KR 10-2015-0028661 A 3/2015
(Continued)

OTHER PUBLICATIONS

Lee, Seo-Hyun, Young-Eun Lee, and Seong-Whan Lee. "Voice of Your Brain: Cognitive Representations of Imagined Speech, Overt Speech, and Speech Perception Based on EEG." arXiv preprint arXiv:2105.14787 (May 31, 2021).

*Primary Examiner* — Hee K Song
(74) *Attorney, Agent, or Firm* — NSIP Law

(57) ABSTRACT

One embodiment of the user authentication method using brainwave signal according to imagined speech includes extracting and storing characteristic information of a first brainwave signal generated by an imagined speech of a first user based on preset imagined speech induction information provided to the first user by the user authentication apparatus, and determining whether a second user matches the first user by extracting characteristic information of a second brainwave signal generated by an imagined speech of the second user, based on preset imagined speech induction information provided to the second user, comparing the characteristic information of the first brainwave signal with the characteristic information of the second brainwave signal stored according to the extracting and storing, and analyzing a result of the comparing by the user authentication apparatus.

19 Claims, 5 Drawing Sheets

(51) Int. Cl.
*A61B 5/117* (2016.01)
*A61B 5/374* (2021.01)
*A61B 5/378* (2021.01)
*A61B 5/38* (2021.01)
*G06F 3/01* (2006.01)

(52) U.S. Cl.
CPC .............. *A61B 5/38* (2021.01); *A61B 5/7267* (2013.01); *G06F 3/015* (2013.01)

(56) References Cited

U.S. PATENT DOCUMENTS

| | | | |
|---|---|---|---|
| 2019/0107888 A1* | 4/2019 | Sereshkeh | A61B 5/374 |
| 2019/0332751 A1* | 10/2019 | Brady | G06V 10/761 |
| 2020/0159902 A1* | 5/2020 | Noh | A61B 5/117 |
| 2021/0031778 A1* | 2/2021 | Farooq | G06F 21/32 |

FOREIGN PATENT DOCUMENTS

| | | |
|---|---|---|
| KR | 10-1607432 B1 | 3/2016 |
| KR | 10-2019-0096780 A | 8/2019 |
| KR | 10-2020-0052807 A | 5/2020 |
| KR | 10-2021-0064924 A | 6/2021 |

* cited by examiner

USER AUTHENTICATION APPARATUS AND METHOD USING BRAINWAVE SIGNAL ACCORDING TO IMAGINED SPEECH

CROSS-REFERENCE TO RELATED APPLICATIONS

The present application claims priority under 35 U.S.C 119(a) to Korean Patent Application No. 10-2021-0079992, filed on Jun. 21, 2021, which is incorporated herein by reference in its entirety.

BACKGROUND

1. Technical Field

The present disclosure relates to a user authentication apparatus and a user authentication method using a brainwave signal according to an imagined speech, and more particularly, to a user authentication apparatus and a user authentication method for authenticating a user by extracting and classifying characteristics of a brainwave signal generated as a user performs an imagined speech.

2. Related Art

The known brain-machine interface technology measures signals generated by activity of nerve cells occurring in the brain and controls an output device only with brainwave signals without a separate input device. The brain-machine interface recognizes user's intention by inducing a specific brainwave signal pattern, such as, motor imagery (MI), steady state evoked potential (SSEP), event related potential (ERP), and imagined speech. Among these, an imagined speech relates to a brainwave signal generated in a specific pattern in Broca's area having a function of speaking when a user imagines speaking, and Wernicke's area having a function of language interpretation. The imagined speech is to imagine things like speaking without moving an articulatory organ and without making a sound. Therefore, the imagined speech does not require external stimuli and has an advantage of illustrating prominent characteristics for each user compared to other endogenous brain-computer interface paradigms. Accordingly, this imagined speech-based brain-machine interface may be used as a communication system and personal authentication system for patients with speech disabilities or ordinary persons.

In order to acquire brainwaves, it is generally required to first coat the scalp with a cap to which multiple electrodes such as 64 electrodes or 32 electrodes are attached and a gel which increases electrical conductivity. This brainwave acquisition method has a disadvantage in that it takes a long time to wear the cap and the gel is applied to the hair, resulting in great reduction in utility in real life. In addition, a method of acquiring brainwaves from a small number of channels is more convenient than the method of obtaining brainwaves from multiple channels, thereby being a brainwave measurement method that may be used in real life. However, since the method of acquiring brainwaves by using a small number of channels has a problem of performance degradation due to spatial information loss, brainwaves acquired from multiple channels are mainly used in the known brain-computer interface system.

In addition, personal authentication uses a user's unique physical characteristics. Just as fingerprints are different for each person, each person's brainwave signals are different, and thus, by utilizing brainwave signals among the user's individual biological signal, a brainwave signal-based personal authentication method may be implemented. Distinct brainwave characteristics of each of several users represent a greater difference than the brainwave characteristics that appear when the same user recognizes different intentions. The brainwave signal has an advantage in that possibility of theft is the lowest than other physical characteristics, thereby being used as an effective and safe means of personal authentication.

The known personal authentication technology using a brainwave signal measures and uses a brainwave signal in a resting state. However, the brainwave signal in the resting state has a limitation in that a pattern for each user does not illustrate a clear difference. In other words, although there are user-specific patterns in the brainwave signal in the resting state, a difference between the patterns is not great, and when the brainwave signal in the resting state is used for self-authentication technology, user recognition performance may be reduced. Therefore, there is need for a method of self-authentication using a brainwave signal that may increase user convenience and reliability by acquiring a corresponding brainwave signal from a small number of channels rather than multiple channels while using a brainwave signal indicating a clear difference in patterns for each user.

SUMMARY

The present disclosure is to solve the above problems and provides, as one technical object, an apparatus and a method for authenticating a user by extracting and classifying characteristics of a brainwave signal generated as a user performs an imagined speech.

The technical objects to be achieved by the present disclosure are not limited to the above technical objects, and other technical objects of the present disclosure may be derived from the following descriptions.

One embodiment of the present disclosure provides a user authentication method implemented through communication connection between a brainwave measurement device for measuring a brainwave signal according to an imagined speech and a user authentication apparatus. The method includes extracting and storing characteristic information of a first brainwave signal generated by an imagined speech of a first user based on preset imagined speech induction information provided to the first user by the user authentication apparatus, and determining whether a second user matches the first user by extracting characteristic information of a second brainwave signal generated by an imagined speech of the second user, based on preset imagined speech induction information provided to the second user, comparing the characteristic information of the first brainwave signal with the characteristic information of the second brainwave signal stored according to the extracting and storing, and analyzing a result of the comparing by the user authentication apparatus.

Another embodiment of the present disclosure provides a user authentication apparatus using a brainwave measurement device for measuring brainwave signals according to an imagined speech. The user authentication apparatus includes the brainwave measurement device including one brainwave signal measurement channel and disposed in a region around an ear of a user to measure the brainwave signals according to an imagined speech of the user, a communication module configured to receive measured brainwave signals from the brainwave measurement device, a memory storing a user authentication program using the brainwave signals, and a processor configured to execute the user authentication program using the brain wave signals stored in the memory, wherein the processor provides preset imagined speech induction information to a first user, receives a first brainwave signal according to an imagined speech of the first user performed based on the preset imagined speech induction information from the brainwave measurement device through the communication module, extracts and stores characteristic information of the first brainwave signal, and performs user classification, and the processor provides preset imagined speech induction information to a second user, receives a second brainwave signal according to an imagined speech of the second user performed based on the preset imagined speech induction information from the brainwave measurement device through the communication module, extracts characteristic information of the first brainwave signal, compares the characteristic information of the first brainwave signal with the characteristic information of the second brainwave signal, analyzes a result of the comparison, and determines whether the second user matches the first user.

BRIEF DESCRIPTION OF THE DRAWINGS

Various embodiments of the present disclosure will become more apparent in view of the attached drawings and accompanying detailed description, in which.

DETAILED DESCRIPTION OF THE EMBODIMENTS

Figure 1:
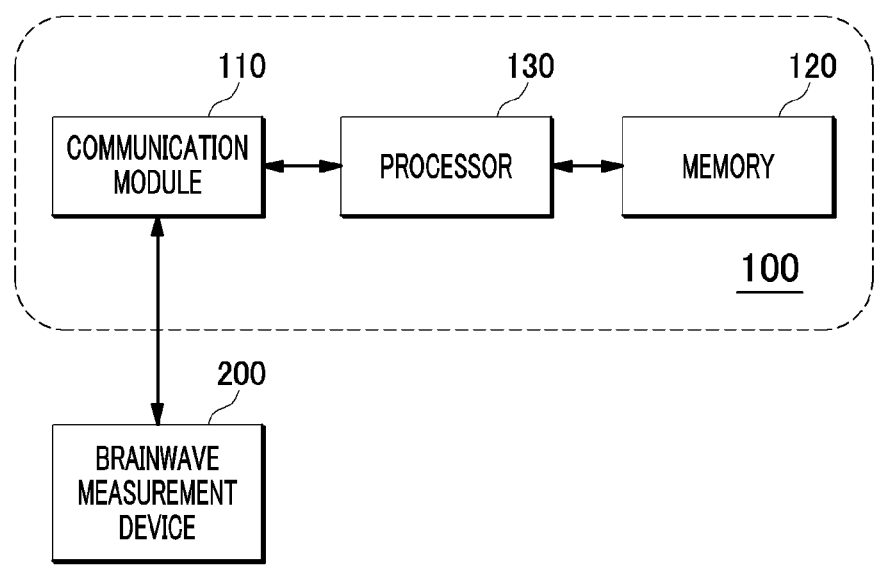
FIG. 1 is a block diagram illustrating a configuration of a user authentication apparatus using a brainwave signal according to an imagined speech and a brainwave measurement device according to an embodiment of the present disclosure.

Hereinafter, the present disclosure will be described in detail with reference to the accompanying drawings. However, the present disclosure may be implemented in various different forms and is not limited to the embodiments described herein. In addition, the accompanying drawings are only for easy understanding of the embodiments disclosed in the present specification, and the technical ideas disclosed in the present specification are not limited by the accompanying drawings. In order to clearly describe the present disclosure in the drawings, portions irrelevant to the description are omitted, and a size, a shape, and a shape of each component illustrated in the drawings may be variously modified. The same/similar reference numerals are attached to the same/similar portions throughout the specification.

Suffixes "module" and "portion" for components used in the following description are given or mixed in consideration of only ease of describing the specification and do not have distinct meanings or functions by themselves. In addition, in describing the embodiments disclosed in the present specification, when it is determined that detailed descriptions of related known technologies may obscure the gist of the embodiments disclosed in the present specification, detailed descriptions thereof are omitted.

Throughout the specification, when a portion is described to be "connected (coupled, in contact, or combined)" to or with another portion, this means not only "directly connected (coupled, in contact, or combined)" but also "indirectly connected (coupled, in contact, or combined)" with another member therebetween. Also, when a portion "includes (comprises or is provided with)" a component, it does not exclude other components unless otherwise stated but may further "includes (comprises or is provided with)" other components.

Terms indicating an ordinal number such as first, second, and so on used herein are used only for the purpose of distinguishing one element from another, and do not limit an order or relationship of components. For example, the first component of the present disclosure may be referred to as the second component, and similarly, the second component may also be referred to as the first component.

FIG. 1 illustrates a configuration of a user authentication apparatus (hereinafter, referred to as a "user authentication apparatus 100") using a brainwave signal according to an imagined speech according to an embodiment of the present disclosure and a brainwave measurement device 200 connected to the user authentication apparatus.

Referring to FIG. 1, the user authentication apparatus 100 includes a communication module 110, a memory 120, and a processor 130. The user authentication apparatus 100 may be implemented as an apparatus that may access a server or a terminal through a network. In addition, the user authentication apparatus 100 may be implemented in the form of an electronic security system. The brainwave measurement device 200 includes one brainwave signal measurement channel and is disposed in a region around a user's ear to measure a brainwave signal according to a user's imagined speech. The brainwave measurement device 200 will be described in more detail with reference to FIG. 2.

The communication module 110 receives a brainwave signal measured from the brainwave measurement device 200. The communication module 110 may include a device including hardware and software necessary for transmitting and receiving a signal such as a control signal or a data signal through wired/wireless connection with other network devices. A network may be implemented as any kind of wireless network, for example, a wired network such as a local area network (LAN), a wide area network (WAN), or a value added network (VAN), a mobile radio communication network, a satellite network, or so on.

The memory 120 stores a user authentication program using a brainwave signal. The user authentication program using the brainwave signal is named for the sake of convenience of description and may be named with another name, and a function of the program is not limited by the name itself. The memory 120 may store at least one of data input to the communication module 110, data required for a function performed by the processor 130, and data generated according to an operation of the processor 130. The memory 120 should be interpreted as a generic term for a non-volatile memory device that continuously maintains the stored information even when power is not supplied, and a volatile memory device that requires power to maintain the stored information. In addition, the memory 120 may perform a function of temporarily or permanently storing data processed by the processor 130. The memory 120 may include a magnetic storage medium or a flash storage medium in addition to the volatile memory device that requires power to maintain the stored information, but the scope of the present disclosure is not limited thereto.

The processor 130 executes a user authentication program using a brainwave signal stored in the memory 120. The processor 130 may include various types of devices for controlling and processing data. The processor 130 may refer to a data processing device which is embedded in hardware and includes a physically structured circuit to perform a function expressed as a code or an instruction included in a program. In one example, the processor 140 may include a microprocessor, a central processing unit (CPU), a processor core, a multiprocessor, an application-specific integrated circuit (ASIC), or a field programmable gate array (FPGA), but the scope of the present disclosure is not limited thereto.

The processor 130 may execute a user authentication program using a brainwave signal to perform the following functions.

First, the processor 130 may provide preset imagined speech induction information to a first user. The processor 130 may receive a first brainwave signal according to an imagined speech of a first user, based on the preset imagined speech induction information from the brainwave measurement device 200 through the communication module 110. The processor 130 may perform user classification by extracting and storing characteristic information of the first brainwave signal. Here, the preset imagined speech induction information may include at least one of auditory information and visual information on a language composed of at least one character. The first brainwave signal may be a signal of a specific pattern generated in at least one of a Broca's brain area and a Wernicke's brain area of the first user measured by the brainwave measurement device 200.

Next, the processor 130 may provide the preset imagined speech induction information to the second user. The processor 130 may receive a second brainwave signal according to an imagined speech of a second user, based on the preset imagined speech induction information from the brainwave measurement device 200 through the communication module 110. The processor 130 may determine whether the second user matches the first user by extracting characteristic information of the second brainwave signal and comparing the characteristic information of the first brainwave signal with the characteristic information of the second brainwave signal and analyzing a result of the comparing. Here, the second brainwave signal may be a signal of a specific pattern generated in at least one of Broca's brain area and Wernicke's brain area of the second user measured by the brainwave measurement device 200.

Furthermore, the processor 130 executes a user authentication program by using a brainwave signal, and the user authentication apparatus 100 may provide a guide voice for the preset imaged speech induction information or visually display a guide phrase for the preset imaged speech induction information such that a first user performs an imaged speech according to the preset imaged speech induction information. In addition, the processor 130 may extract characteristic information including time-frequency characteristics of a first brainwave signal received from the brainwave measurement device 200 through the communication module 110 by utilizing a deep learning model designed to extract and classify the time-frequency characteristics of brainwave signals, and further perform user classification based on the extracted characteristic information.

The processor 130 executes a user authentication program by using a brainwave signal, the user authentication apparatus 100 may provide a guide voice for the preset imaged speech induction information or visually display a guide phrase for the preset imaged speech induction information such that a second user performs an imaged speech according to the preset imaged speech induction information. In addition, the processor 130 may extract characteristic information including time-frequency characteristics of a second brainwave signal transmitted from the brainwave measurement device 200 through the communication module 110 by utilizing a deep learning model designed to extract and classify the time-frequency characteristics of brainwave signals and may perform user classification based on the extracted characteristic information.

The processor 130 may evaluate similarity between the characteristic information of the first brainwave signal and the characteristic information of the second brainwave signal by executing the user authentication program by using a brainwave signal and may determines that the second user matches the first user when the similarity is greater than or equal to a preset value and may determine that the second user does not match the first user when the similarity is less than a preset value. For example, the similarity between the first brainwave signal and the second brainwave signal may be evaluated based on a time-frequency graph of each brainwave signal. Accordingly, when the similarity is greater than or equal to a specific value, it is determined that the second user matches the first user, and thereby, user authentication may be performed.

Figure 2:
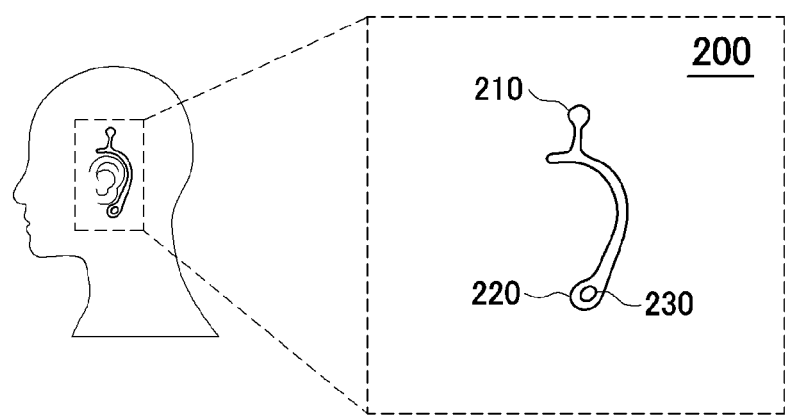
FIG. 2 is a view illustrating a detailed configuration of the brainwave measurement device illustrated in FIG. 1.

FIG. 2 is a view illustrating a detailed configuration of the brainwave measurement device 200. Referring to FIG. 2, the brainwave measurement device 200 includes a single brainwave signal measurement channel 210 and may further include a reference channel 220 and a communication module 230. In addition, the brainwave measurement device 200 may have a structure detachable from an ear region. For example, the brainwave measurement device 200 may be worn on a left ear pinna. The brainwave signal measurement channel 210 may measure signals generated in the Broca's brain area and the Wernicke's brain area existing in the left temporal lobe. The reference channel 220 may generate a signal of a constant pattern and intensity, and accordingly, the brainwave measurement device 200 may acquire a brainwave signal according to a difference between a signal acquired from the brainwave signal measurement channel 210 and a signal of the reference channel 220. The communication module 230 may transmit the acquired brainwave signal to an external device. Here, the external device may be the user authentication apparatus 100 described above.

Hereinafter, an embodiment of a user authentication method will be described in detail by using the user authentication apparatus 100.

The user authentication apparatus 100 repeatedly collects brainwaves in a resting state and brainwaves according to induction of an auditory or visual imagined speech from the brainwave measurement device 200 while a user wears the brainwave measurement device 200. For example, the user authentication apparatus 100 acquires a 2-second resting state brainwaves from the brainwave measurement device 200, and then provides information on a class to perform imagined speech according to auditory or visual imagined speech induction information for 2 seconds. For subsequent 2 seconds, the user performs an imagined speech for a given class, the brainwave measurement device 200 measures brainwaves in this section, and the user authentication apparatus 100 collects the brainwaves measured by the brainwave measurement device 200. The user authentication apparatus 100 may collect imagined speech brainwaves for each user by repeating the above process n times.

By arranging the brainwave measurement device 200 having a single channel in the Broca-Wernicke's areas where brainwaves of the imagined speech are characteristically generated, the user authentication apparatus 100 may collect brainwave signals measured by the brainwave measurement device 200. For example, the brainwave measurement device 200 may collect brainwave signals by setting a sampling frequency to a frequency of 1000 Hz, but a channel position and the sampling frequency are not fixed and may vary depending on circumstances. When the brainwave signal collected by the brainwave measurement device 200 includes noise such as eye blinking, the user authentication apparatus 100 may remove the noise through a pre-processing process. The user authentication apparatus 100 may extract, by utilizing time-frequency characteristics, brainwave characteristics generated when a user performs an imagined speech.

The user authentication apparatus 100 may perform user authentication through a user registration step and a secret phrase setting and use step. The user registration step may be a process of collecting and registering a brainwave for each user when performing a given class and free imagined speech. The use step may be a process of identifying whether a user who wants user authentication is a user in a previously registered database.

The user authentication apparatus 100 may first collect imagined speech brainwaves for each user in order to store and register user-specific characteristics appearing in the brainwaves. The process of collecting the imagined speech brainwaves for each user may include a process of providing an auditory cue to perform an imagined speech for a specific class and a process of collecting user's free imagined speech brainwaves. A class that performs an imagined speech may include phoneme units such as "ah", "uh", and "u", words such as "hello" and "apple", and a sentence unit such as "user authentication is requested".

A process of measuring brainwaves of an imagined speech for a specific class may include a process of extracting and storing brainwave of an imagined speech for 2 seconds after a user wearing the EEG measuring device 200 hears a voice of the above class, guide voice such as "perform an imagined speech for a voice you heard after a beep", and a beep sound. A process of collecting a user's secret phrase brainwaves may include a process of collecting and storing brainwaves of an imagined speech for a specific time period such as 2 seconds after a guide voice such as "perform an imagined speech of a secret phrase after a beep sound" and the beep sound. This process may be a process of strengthening security by setting a secret phrase for each user, similarly to the process of registering each user's voice in voice recognition.

The user authentication apparatus 100 may extract and classify time-frequency characteristics based on deep learning by using the collected brainwave signals. The time-frequency characteristics designate a convolution kernel in association with a sampling frequency of the brainwaves. That is, the convolution kernel is set to a size related to the sampling frequency in order to consider frequency characteristics. The convolution kernel is extracted as a single characteristic vector through several convolutional layers. For example, the convolution kernel may be set to ½ or ¼ of the sampling frequency.

The user authentication apparatus 100 may form a fully-connected classifier composed of hinge loss by using a user's individual imagined speech characteristics extracted through the convolutional kernel. In other words, a user classifier may be configured by a machine learning classifier of a user category based on a set including pre-extracted characteristic vectors. The machine learning classifier may include a support vector machine and a fully-connected layer composed of hinge loss.

The user authentication apparatus 100 may derive a personal authentication result based on a classifier formed by using brainwaves of an imagined speech collected during individual authentication of each user through the personal authentication process. The user authentication apparatus 100 may collect brainwaves of an imagined speech of a use, extract time-frequency characteristics based on the previous convolution layer, and perform user classification based on a previous classifier. The user authentication apparatus 100 may determine whether the user is a registered user by classifying each individual through a classifier based on the derived result. The user authentication apparatus 100 may transmit a command for unlocking by sending information to a safe, a security system, or so on in which the user authentication apparatus 100 is installed, based on the derived personal authentication result.

The user authentication apparatus 100 may perform a user registration process, a secret phrase setting process, and a personal authentication process. The user registration process may include four processes. The user registration process and the secret phrase setting process may include a process of inducing various imagined speeches for user registration as a process of inducing an imagined speech for registration. In addition, the user registration process includes a process of acquiring a user's brainwave signal from the brainwave measurement device 200. The user registration process includes a process of extracting time-frequency characteristics for each user-specific pattern related to an imagined speech from a brainwave signal. The user registration process includes a process of configuring a user classifier based on characteristics previously extracted as a configuration of a user classifier. In this case, a specific secret phrase may be set, and the user classifier may further perform an imagined speech with a word or a phrase that may perform an imagined speech at a specific time such as 2 seconds. In addition, a corresponding phrase may be used for personal authentication.

The personal authentication process may include five processes. The personal authentication process includes a process of inducing an imagined speech for a word designated by a user by inducing the imagined speech. The personal authentication process is a process of collecting brainwaves for personal authentication and may include a process of collecting brainwaves from the brainwave measurement device 200. The personal authentication process is as a process of extracting time-frequency characteristics and may include a process similar to a process of extracting the time-frequency characteristics in the user registration process described above. The personal authentication process is a user classification process and may include a process of classifying a user's brainwaves acquired in the personal authentication process by using the user classifier configured through the user registration process. The personal authentication process is a process of deriving a personal authentication result and may include a process of deriving the personal authentication result according to the previous classification result and transmitting the personal authentication result to a control device.

Figure 3:
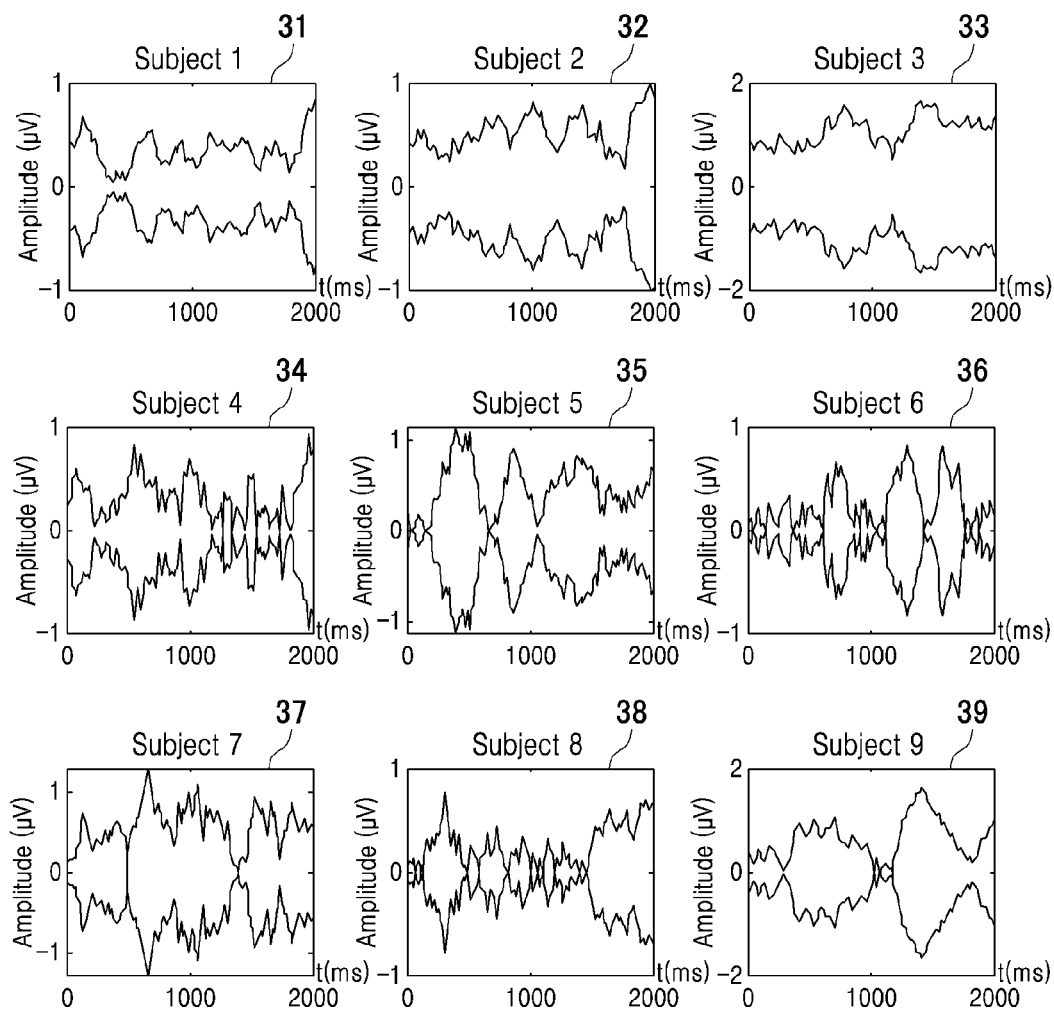
FIG. 3 illustrates examples of brainwave signals of users which are measured through the brainwave measurement device illustrated in FIG. 2.

FIG. 3 illustrates examples of brainwave signals of users measured through the brainwave measurement device illustrated in FIG. 2. Examples 31, 32, 33, 34, 35, 36, 37, 38, and 39 of brainwave signals of users illustrated in FIG. 3 are graphs illustrating envelopes of brainwave signals of different users according to an imagined speech. Here, the envelopes represent characteristics of sound according to a change in time and sound volume, and it may be seen that each user's individual characteristics appear at the time of an imagined speech of each user. In other words, referring to FIG. 3, it may be seen that characteristics of brainwave signals according to an imagined speech of each user are different from each other just as characteristics of voice are different for each person.

Figure 4:
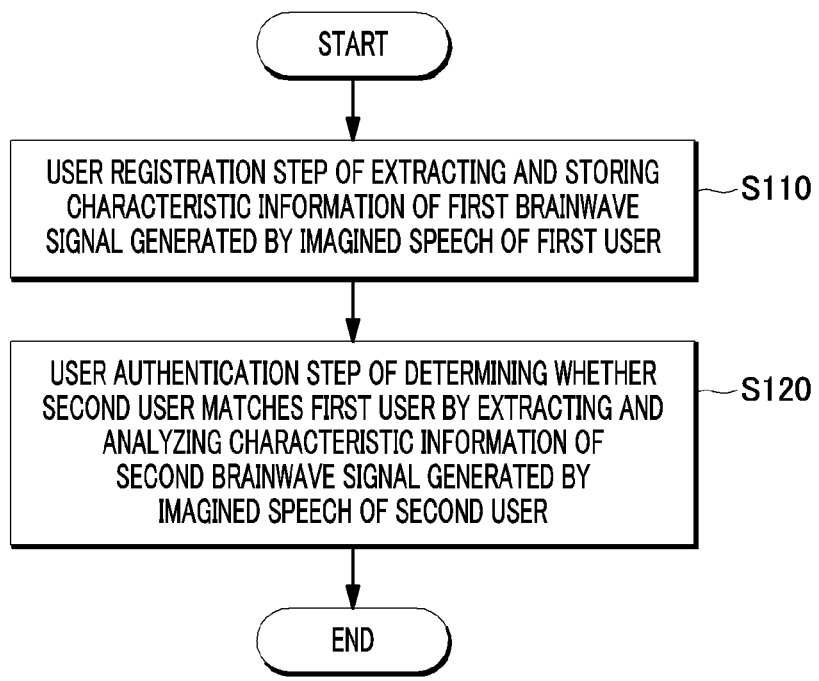
FIG. 4 is a flowchart illustrating a procedure of a user authentication method using a brainwave signal according to an imagined speech, according to another embodiment of the present disclosure.
Figure 5:
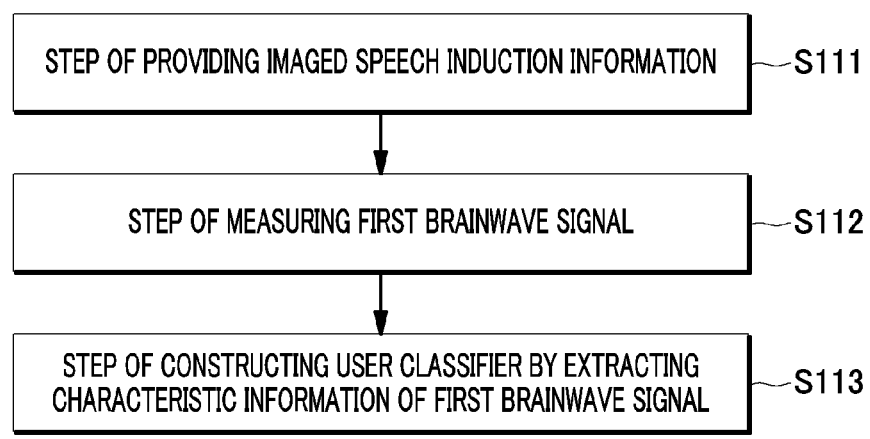
FIGS. 5 and 6 are flowcharts illustrating detailed processes of steps of the user authentication method using the brainwave signal according to the imagined speech illustrated in FIG. 4.
Figure 6:
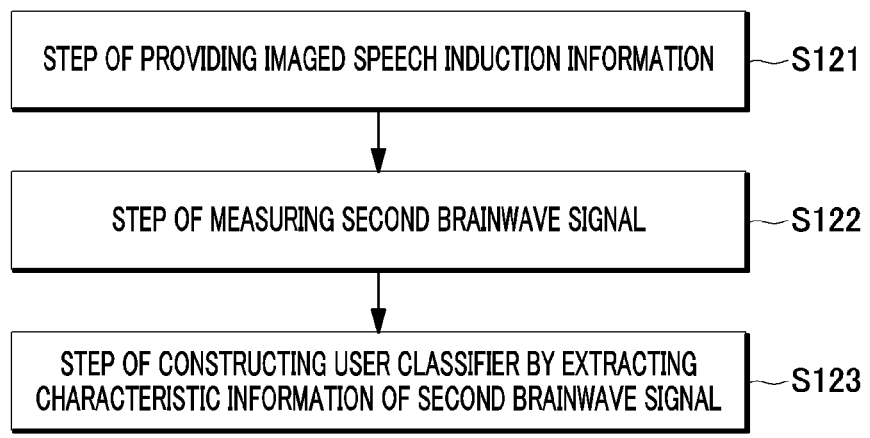

FIG. 4 is a flowchart illustrating a procedure of a user authentication method using a brainwave signal according to an imagined speech, according to another embodiment of the present disclosure, and FIGS. 5 and 6 are flowcharts illustrating detailed processes of steps of the user authentication method using the brainwave signal according to the imagined speech illustrated in FIG. 4. A user authentication method using a brainwave signal, according to an imagined speech to be described below may be performed by using the user authentication apparatus 100 and the brainwave measurement device 200 described above. Accordingly, contents overlapping the above-described contents are omitted hereinafter. In addition, descriptions of the user authentication apparatus 100 and the brainwave measurement device 200 described above with reference to FIGS. 1 to 3 may be equally applied to a user authentication method using a brainwave signal, according to a following imagined speech.

Referring to FIG. 4, a user authentication method using a brainwave signal, according to an imagined speech includes a user registration step S110 and a user authentication step S120. In the user registration step S110, the user authentication apparatus 100 extracts and stores characteristic information of a first brainwave signal generated by an imagined speech of a first user, based on preset imagined speech induction information provided to the first user. In the user authentication step S120, the user authentication apparatus 100 extracts characteristic information of a second brainwave signal generated by an imagined speech of a second user, based on preset imagined speech induction information provided to the second user, compares the characteristic information of the first brainwave signal with the characteristic information of the second brainwave signal stored according to the user registration step, analyzes a result of the comparison, and determines whether the second user matches the first user. In the user authentication step S120, the user authentication apparatus 100 evaluates similarity between the characteristic information of the first brainwave signal and the characteristic information of the second brainwave signal, and determines that the second user matches the first user when the similarity is greater than or equal to a preset value, and determines that the second user does not match the first user when the similarity is less than the preset value.

The preset imagined speech induction information may include at least one of auditory information and visual information on a language composed of at least one character. The first brainwave signal includes one brainwave signal measurement channel and may be a signal of a specific pattern generated in at least one of a Broca's brain area and a Wernicke's brain area of the first user measured by the brainwave measurement device 200 disposed in a region around an ear of the first user. The second brainwave signal may be a signal of a specific pattern generated in at least one of a Broca's brain area and a Wernicke's brain area of the second user measured by the brainwave measurement device 200 disposed in a region around an ear of the second user.

Referring to FIG. 5, a user registration step S110 may include a step S111 of providing preset imaged speech induction information to a first user by the user authentication apparatus 100, a step S112 of measuring a first brainwave signal according to an imagined speech of a first user, based on the preset imaged speech induction information by the brainwave measurement device 200, and a step S113 of constructing a user classifier by receiving the first brainwave signal from the brainwave measurement device 200 and extracting and storing characteristic information of the first brainwave signal by the user authentication apparatus 100.

The step S111 may include a step of providing a guide voice for the preset imaged speech induction information or visually display a guide phrase for the preset imaged speech induction information by using the user authentication apparatus 100 such that a first user performs an imaged speech according to the preset imaged speech induction information. The step S112 may include a step of collecting and storing the first brainwave signal for a specific time, according to an imagined speech of the first user, based on the preset imaged speech induction information by using the brainwave measurement device 200 and transmitting the first brainwave signal to the user authentication apparatus 100. The step S113 may include a step of extracting characteristic information including time-frequency characteristics of the first brainwave signal transmitted from the brainwave measurement device 200 by the user authentication apparatus 100 by utilizing a deep learning model designed to extract and classify the time-frequency characteristics of brainwave signals, and constructing a user classifier based on the extracted characteristic information.

Referring to FIG. 6, the user authentication step S120 may include a step S111 of providing preset imaged speech induction information to a second user by the user authentication apparatus 100, a step S122 of measuring a second brainwave signal according to an imagined speech of a second user, based on the preset imaged speech induction information by the brainwave measurement device 200, and a step S123 of determining whether the second user matches the first user by receiving the second brainwave signal from the brainwave measurement device 200, extracting characteristic information of the second brainwave signal, comparing the characteristic information of the second brainwave signal with the characteristic information of the first brainwave signal, and analyzing a result of the comparing by the user authentication apparatus 100.

The step S121 may include a step of providing a guide voice for the preset imaged speech induction information or visually display a guide phrase for the preset imaged speech induction information by using the user authentication apparatus 100 such that the second user performs an imaged speech according to the preset imaged speech induction information. The step S122 may include a step of collecting and storing the second brainwave signal for a specific time, according to an imagined speech of the second user, based on the preset imaged speech induction information and transmitting the second brainwave signal to the user authentication apparatus 100 by using the brainwave measurement device 200. The step S113 may include a step of extracting characteristic information including time-frequency characteristics of the second brainwave signal transmitted from the brainwave measurement device 200 by the user authentication apparatus 100 by utilizing a deep learning model designed to extract and classify the time-frequency characteristics of first brainwave signals, and performing user classification and user authentication based on the extracted characteristic information.

The above steps may be performed according to a determined order but are not limited thereto, and for example, the respective steps may be performed simultaneously or in an order different from the determined order. Also, an event-based object tracking method in which some steps are omitted may be performed.

The user authentication method using the brain wave signal according to the imagined speech described above may also be implemented in the form of a recording medium including instructions executable by a computer such as a program module to be executed by a computer. A computer-readable medium may be any available media that may be accessed by a computer and includes all of volatile and nonvolatile media, and removable and non-removable media. Also, the computer-readable medium may include a computer storage medium. The computer storage medium includes all of volatile and nonvolatile media, and removable and non-removable media implemented in any method or technology for storing information such as computer readable instructions, data structures, program modules or other data.

Those skilled in the art to which the present disclosure pertains will be able to understand that the present disclosure may be easily modified into other specific forms without changing the technical idea or essential characteristics of the present disclosure based on the above description. Therefore, it should be understood that the embodiments described above are illustrative in all respects and not restrictive. The scope of the present disclosure is indicated by the following claims, and all changes or modifications derived from the meaning and scope of the claims and their equivalent concepts should be construed as being included in the scope of the present disclosure.

The scope of the present application is indicated by the following claims rather than the above detailed description, and all changes or modifications derived from the meaning and scope of the claims and their equivalent concepts should be construed as being included in the scope of the present application.

According to the present disclosure, an apparatus and method for self-authentication may be implemented by using a brainwave signal at the time of an imagined speech in which a user's specific pattern is strongly generated without an external stimulus.

In addition, according to the present disclosure, a user's convenience may be increased by acquiring a brainwave signal by using only a single channel or a small number of channels around an ear.

In addition, according to the present disclosure, by using time-frequency mixing characteristics in extracting characteristics of a brainwave signal for each user, more prominent characteristics of the brainwave signal may be extracted compared to when frequency characteristics are used.

In addition, according to the present disclosure, an apparatus and a method for self-authentication that may not be illegally used may be implemented by using a characteristic pattern of a unique user-specific brainwave signal that is generated when a user performs an imagined speech.

Effects of the present disclosure are not limited to the above-described effects and include all effects understood from the following descriptions.

What is claimed is:

1. A user authentication method implemented through communication connection between a brainwave measurement device for measuring a brainwave signal according to an imagined speech and a user authentication apparatus, the user authentication method comprising:

extracting and storing characteristic information of a first brainwave signal generated by an imagined speech of a first user based on preset imagined speech induction information provided to the first user by the user authentication apparatus; and determining whether a second user matches the first user by extracting characteristic information of a second brainwave signal generated by an imagined speech of the second user, based on preset imagined speech induction information provided to the second user, comparing the characteristic information of the first brainwave signal with the characteristic information of the second brainwave signal stored according to the extracting and storing, and analyzing a result of the comparing by the user authentication apparatus, wherein the determining comprises evaluating similarity between the characteristic information of the first brainwave signal and the characteristic information of the second brainwave signal based on a time-frequency graph of each brainwave signal, and wherein each brainwave signal is acquired by using only a single brainwave signal measurement channel.

2. The user authentication method of claim 1, wherein the preset imagined speech induction information includes at least one of auditory information and visual information on a language composed of at least one character.

3. The user authentication method of claim 1, wherein the first brainwave signal includes one brainwave signal measurement channel and is a signal of a specific pattern generated in at least one of a Broca's brain area and a Wernicke's brain area of the first user measured by the brainwave measurement device disposed in a region around an ear of the first user, and wherein the second brainwave signal is a signal of a specific pattern generated in at least one of a Broca's brain area and a Wernicke's brain area of the second user measured by the brainwave measurement device disposed in a region around an ear of the second user.

4. The user authentication method of claim 1, wherein the extracting and storing includes:

providing, by the user authentication apparatus, the preset imagined speech induction information to the first user, measuring, by the brainwave measurement device, the first brainwave signal according to the imagined speech of the first user, based on the preset imagined speech induction information, and constructing a user classifier by receiving the first brainwave signal from the brainwave measurement device and extracting and storing the characteristic information of the first brainwave signal by the user authentication apparatus.

5. The user authentication method of claim 4, wherein the providing includes:

providing a guide voice for the preset imaged speech induction information or visually displaying a guide phrase for the preset imaged speech induction information by the user authentication apparatus such that the first user performs an imaged speech according to the preset imaged speech induction information.

6. The user authentication method of claim 4, wherein the measuring includes:
  collecting and storing the first brainwave signal for a specific time, according to the imagined speech of the first user, based on the preset imagined speech induction information, and
  transmitting the first brainwave signal to the user authentication apparatus by the brainwave measurement device.

7. The user authentication method of claim 4, wherein the constructing includes:
  extracting characteristic information including time-frequency characteristics of the first brainwave signal transmitted from the brainwave measurement device by the user authentication apparatus by utilizing a deep learning model designed to extract and classify time-frequency characteristics of brainwave signals, and
  constructing a user classifier based on the extracted characteristic information.

8. The user authentication method of claim 1, wherein the determining includes:
  providing, by the user authentication apparatus, the preset imagined speech induction information to the second user,
  measuring, by the brainwave measurement device, the second brainwave signal according to an imagined speech of the second user, based on the preset imagined speech induction information, and
  determining whether the second user matches the first user by receiving the second brainwave signal from the brainwave measurement device,
  extracting the characteristic information of the second brainwave signal,
  comparing the characteristic information of the second brainwave signal with the characteristic information of the first brainwave signal, and
  analyzing a result of the comparing by the user authentication apparatus.

9. The user authentication method of claim 8, wherein the providing includes:
  providing a guide voice for the preset imaged speech induction information or visually display a guide phrase for the preset imaged speech induction information by the user authentication apparatus such that the second user performs an imaged speech according to the preset imaged speech induction information.

10. The user authentication method of claim 8, wherein the measuring includes:
  collecting and storing the second brainwave signal for a specific time, according to the imagined speech of the second user, based on the preset imagined speech induction information, and
  transmitting the second brainwave signal to the user authentication apparatus by the brainwave measurement device.

11. The user authentication method of claim 8, wherein the determining includes:
  extracting the characteristic information including time-frequency characteristics of the second brainwave signal transmitted from the brainwave measurement device by utilizing a deep learning model designed to extract and classify the time-frequency characteristics of first brainwave signals, and
  performing user classification and user authentication based on the extracted characteristic information by the user authentication apparatus.

12. The user authentication method of claim 1, wherein the determining includes:
  determining that the second user matches the first user when the similarity is greater than or equal to a preset value, and
  determining that the second user does not match the first user when the similarity is less than the preset value.

13. A user authentication apparatus using a brainwave measurement device for measuring brainwave signals according to an imagined speech, the user authentication apparatus comprising:
  the brainwave measurement device including one brainwave signal measurement channel and disposed in a region around an ear of a user to measure the brainwave signals according to an imagined speech of the user;
  a communication module comprising network devices including hardware and software configured to receive measured brainwave signals from the brainwave measurement device;
  a memory storing a user authentication program using the brainwave signals; and
  a processor configured to:
    execute the user authentication program using the brain wave signals stored in the memory,
    provide preset imagined speech induction information to a first user,
    receive a first brainwave signal according to an imagined speech of the first user performed based on the preset imagined speech induction information from the brainwave measurement device through the communication module,
    extract and store characteristic information of the first brainwave signal, and
    perform user classification, and
  wherein the processor is configured to:
    provide preset imagined speech induction information to a second user,
    receive a second brainwave signal according to an imagined speech of the second user performed based on the preset imagined speech induction information from the brainwave measurement device through the communication module,
    extract characteristic information of the second brainwave signal,
    compare the characteristic information of the first brainwave signal with the characteristic information of the second brainwave signal,
    analyze a result of the comparison, and
    determine whether the second user matches the first user by evaluating similarity between the characteristic information of the first and second brainwave signals based on a time-frequency graph of each brainwave signal,
  wherein each brainwave signal is acquired by using only a single brainwave signal measurement channel.

14. The user authentication apparatus of claim 13, wherein the preset imagined speech induction information includes at least one of auditory information and visual information on a language composed of at least one character.

15. The user authentication apparatus of claim 13, wherein the first brainwave signal is a signal of a specific pattern generated in at least one of a Broca's brain area and a Wernicke's brain area of the first user measured by the brainwave measurement device, and
  wherein the second brainwave signal is a signal of a specific pattern generated in at least one of a Broca's brain area and a Wernicke's brain area of the second user measured by the brainwave measurement device.

16. The user authentication apparatus of claim 13, wherein the processor executes the user authentication program using the brain wave signals,
wherein the user authentication apparatus provides a guide voice for the preset imaged speech induction information or visually displays a guide phrase for the preset imaged speech induction information such that the first user performs an imaged speech according to the preset imaged speech induction information, and
wherein the processor extracts characteristic information including time-frequency characteristics of the first brainwave signal received from the brainwave measurement device through the communication module by utilizing a deep learning model designed to extract and classify time-frequency characteristics of brainwave signals and further perform user classification based on the extracted characteristic information.

17. The user authentication apparatus of claim 13,
wherein the processor executes the user authentication program using the brain wave signal,
wherein the user authentication apparatus provides a guide voice for the preset imaged speech induction information or visually displays a guide phrase for the preset imaged speech induction information such that the second user performs an imaged speech according to the preset imaged speech induction information, and
wherein the processor extracts characteristic information including time-frequency characteristics of the first brainwave signal received from the brainwave measurement device through the communication module by utilizing a deep learning model designed to extract and classify time-frequency characteristics of brainwave signals and performs user classification and user authentication based on the extracted characteristic information.

18. The user authentication apparatus of claim 13, wherein the processor is configured to:
determine that the second user matches the first user when the similarity is greater than or equal to a preset value, and
determine that the second user does not match the first user when the similarity is less than the preset value.

19. A non-transitory computer-readable recording medium comprising:
a computer program for performing the user authentication method using the brainwave signal according to the imagined speech, according to claim 1.

* * * * *